(12) United States Patent
Roebelt et al.

(10) Patent No.: US 10,390,987 B2
(45) Date of Patent: Aug. 27, 2019

(54) TENSIONING DEVICE FOR ORTHOSES

(71) Applicant: BAUERFEIND AG, Zeulenroda-Triebes (DE)

(72) Inventors: Gerhard Roebelt, Zeulenroda-Triebes (DE); Ronny Baetz, Vogtländisches Oberland (DE); Gerald Stier, Langenwetzendorf (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 222 days.

(21) Appl. No.: 14/398,044

(22) PCT Filed: Apr. 30, 2013

(86) PCT No.: PCT/EP2013/059021
§ 371 (c)(1),
(2) Date: Jan. 28, 2015

(87) PCT Pub. No.: WO2013/164353
PCT Pub. Date: Nov. 7, 2013

(65) Prior Publication Data
US 2015/0133839 A1    May 14, 2015

(30) Foreign Application Priority Data

May 2, 2012   (DE) .................. 10 2012 009 214

(51) Int. Cl.
*A61F 5/01*     (2006.01)
*A61F 5/02*     (2006.01)
(52) U.S. Cl.
CPC .................. *A61F 5/02* (2013.01); *A61F 5/01* (2013.01); *A61F 5/028* (2013.01)

(58) Field of Classification Search
CPC .......... A61F 5/028; A61F 5/0102; A61F 5/02; A61F 5/0193; A61F 5/026; A61F 5/30;
(Continued)

(56) References Cited

U.S. PATENT DOCUMENTS 4,508,110 A    4/1985   Modglin
6,213,968 B1 *  4/2001   Heinz .................... A61F 5/028
                                                        602/19
(Continued)

FOREIGN PATENT DOCUMENTS

CA    2808742 A1 *  2/2012  .............. A61F 5/01
DE    8118318 U1    12/1981
(Continued)

OTHER PUBLICATIONS

Machine translation of DE 102010035309 specification, Espacenet.*
(Continued)

*Primary Examiner* — Alireza Nia
*Assistant Examiner* — Rachel A Berezik
(74) *Attorney, Agent, or Firm* — Stephen T. Olson; Harness, Dickey & Pierce, P.L.C.

(57) ABSTRACT

A tensioning device for orthoses for supporting and maintaining the function of the human body, particularly body-encompassing back orthoses, allows for an individual, segmental adjustment of the supporting effect through individually, separately designed pulley assemblies which can be attached individually and height-adjustably to a backplate designed as central element.

16 Claims, 6 Drawing Sheets

(58) Field of Classification Search
CPC .......... A61F 5/0123; A61F 5/024; A61F 5/01; A61F 2007/0018; A61F 2007/0024–0027; A43C 11/14; A43C 11/16; Y10T 24/37; A41D 13/04; A41D 13/0518; A41D 13/0525; A41D 13/0531
USPC ........ 602/5, 19–27, 60, 62, 63; 128/100, 99, 128/96, 882; 2/311, 319, 467, 310
See application file for complete search history.

(56) References Cited

U.S. PATENT DOCUMENTS

| | | | |
|---|---|---|---|
| 6,322,529 B1* | 11/2001 | Chung | A61F 5/028 2/319 |
| 6,342,044 B1* | 1/2002 | Frangi | A61F 5/028 602/19 |
| 6,478,759 B1* | 11/2002 | Modglin | A61F 5/028 128/100.1 |
| 8,382,693 B1* | 2/2013 | Guldalian | A61F 5/028 602/19 |
| 2002/0068890 A1 | 6/2002 | Schwenn et al. | |
| 2003/0050585 A1* | 3/2003 | Modglin | A61F 5/028 602/19 |
| 2004/0147861 A1 | 7/2004 | Kozersky | |
| 2008/0066272 A1 | 3/2008 | Hammerslag et al. | |
| 2009/0082707 A1 | 3/2009 | Rumsey | |
| 2010/0168630 A1* | 7/2010 | Cropper | A61F 5/024 602/19 |
| 2010/0217167 A1* | 8/2010 | Ingimundarson | A61F 5/028 602/19 |
| 2011/0295169 A1 | 12/2011 | Hendricks | |
| 2012/0004587 A1 | 1/2012 | Nickel et al. | |
| 2012/0101417 A1 | 4/2012 | Joseph | |
| 2013/0211301 A1 | 8/2013 | Stier | |
| 2013/0012856 A1 | 10/2013 | Hammerslag et al. | |

FOREIGN PATENT DOCUMENTS

| | | | |
|---|---|---|---|
| DE | 102010035309 A1 * | 2/2012 | ............... A61F 5/01 |
| DE | 102010035309 A1 | 2/2012 | |
| WO | WO-99/65428 A1 | 12/1999 | |
| WO | 2013/182685 A1 | 12/2013 | |

OTHER PUBLICATIONS

Machine translation of DE 102010035309 claims, Espacenet.*
English Translation of the International Preliminary Report on Patentability (Chapter I) for PCT/EP2013/059021, IB/Geneva, dated Nov. 4, 2014, incorporating the Written Opinion of the ISA, ISA/EP, Munich, dated Jul. 18, 2013.
International Preliminary Report on Patentability for PCT/EP2013/061818 (Chapter II), IPEA, Munich, dated Aug. 19, 2014, with English Translation thereof (incorporating the Written Opinion of the ISA).
International Search Report for PCT/EP2013/061818, ISA/EP, Rijswijk, NL, dated Sep. 30, 2013.
International Search Report for PCT/EP2013/059021, ISA/EP, Rijswijk, NL, dated Jul. 18, 2013.
Written Opinion of the ISA, Munich, dated Jul. 18, 2013.
Notice of Reasons for Rejection regarding Japanese Patent Application No. 2015-509422, dated Aug. 2, 2016. Translation provided by Gleiss & Grosse.

* cited by examiner

TENSIONING DEVICE FOR ORTHOSES

CROSS-REFERENCE TO RELATED APPLICATIONS

This application is a 371 U.S. National Stage of International Application No. PCT/EP2013/059021, filed Apr. 30, 2013. This application claims priority to German Patent Application No. DE 10 2012 009 214.8, filed May 2, 2012. The entire disclosures of the above applications are incorporated herein by reference.

FIELD

The invention relates to a new type of tensioning device for orthoses for supporting and maintaining the function of the human body, particularly body-encompassing back orthoses. The tensioning device allows for an individual, segmental adjustment of the supporting effect through individually, separately designed pulley assemblies which can be attached individually and height-adjustably to a backplate designed as central element.

BACKGROUND

Orthoses are therapeutic appliances for stabilizing or supporting the movement function of body parts, for example, pelvis and spinal column. Orthoses can be used post traumatically, or postoperatively, or conservatively. As a rule, orthoses are applied around the body part, for example around the hip, and closed belt-like such that a stabilizing pressure is applied to the body region to be stabilized. For example, with lumbar orthoses, it might be necessary to immobilize a specific spinal curvature (lordosis) in order to prevent further damage on the spinal column or to stabilize a postoperative condition, thus improving the healing process.

Known orthoses, for example, lumbar orthosis belts, frequently have tensioning devices, with which the tension/pressure of the applied orthosis to the body part can be increased in a controlled manner. For such purpose, a pulley assembly device can be provided. As is known, such a pulley assembly device substantially extends over the entire width of the orthosis with the objective of equalizing the tractive force across the entire width of the orthosis belt. Known tensioning devices which are based on pulley assemblies additionally have a loose pulling cable which runs along one side of the orthosis. It has become apparent that the use of orthoses designed in such a manner is fraught with disadvantages: Due to the equalizing of the tractive force caused by the known pulley assembly mechanism, an individual adjustment of the tension and thus the support effect to an individual treatment goal is not possible. At the same time, the tensioning of known pulley assemblies by means of one-sided pulling cables results in one-sided force action on the orthosis and thus to its warping or slipping.

An improved tensioning device with pulley assemblies is known from DE 10 2010 035 309 A1.

SUMMARY

The invention addresses the problem of further developing and improving tensioning devices for orthoses in order to avoid the known disadvantages. The technical problem addressed by the invention is that of providing an improved tensioning device for an orthosis which can be better adjusted to the requirements of the therapy or prophylaxis, particularly with regard to its support function. In particular, the acting forces are to be directed purposefully and individually toward specific body points, particularly spinal column sections, by means of the orthosis.

The technical problem is solved by a tensioning device according to claim 1.

The technical problem is particularly solved by a tensioning device for an orthosis, having at least one first side element on a first end and at least one second side element on an opposite second end, and at least one central element arranged in between, wherein the first and second side element are connected to one another by means of the central element by means of at least one pulley assembly extending between the central element and the first side element and at least one second pulley assembly extending between the central element and the second side element, wherein the leverage points of the pulley assemblies on the central element are height-adjustable by means of detachable mechanical coupling means.

In a preferred embodiment, the first side element is connected to the central element by means of at least two pulley assemblies, and the second side element is connected to the central element by means of at least two further pulley assemblies, wherein the leverage points of the at least four pulley assemblies on the central element are height-adjustable independently from one another by means of detachable mechanical coupling means.

It has become apparent that the force vectors of an orthosis, particularly, back orthosis, can be aligned individually and purposefully with the location of the back complaints if pulley assemblies are used which can be individually attached height-adjustably on a backplate serving as central element, and so the pulley assemblies can deploy the greatest tensioning effect on the spinal column at the location where they are being attached on the backplate. With a tensioning device according to the invention, it is therefore particularly possible to purposefully and precisely load or relieve specific spinal column sections during treatment of a patient with a back orthosis and thus achieve maximum therapeutic effectiveness.

According to the invention, the pulley assemblies are preferably attached to the central element by means of coupling means. According to the invention, a coupling means preferably comprises a first coupling element and a second coupling element, wherein the first coupling element is located on a pulley assembly and the second element is located on the central element.

According to the invention, the first or second coupling element is preferably a suspension element. According to the invention, the second or first coupling element is preferably a recess.

According to the invention, the pulley assemblies are preferably attached to the central element by mounting suspension elements of the pulley assemblies in recesses of the central element, or by mounting suspension elements of the central element in recesses of the pulley assemblies.

For example, the suspension elements can be latching elements or detent elements. The recesses, for example, can be holes. The holes can have any suitable shape, for example, round or oval. Suitable shapes are known to a person skilled in the art.

In a preferred embodiment, the detachable mechanical coupling means are designed as latching elements or detent elements.

In a preferred embodiment, the coupling elements of the central element are arranged left and right of the region covering the spinal column.

In a preferred embodiment, the leverage points of the at least one first pulley assembly and the at least one second pulley assembly are height-adjustable independently from one another. In a preferred embodiment, the leverage points of all pulley assemblies of the tensioning device are height-adjustable independently from one another.

In a preferred embodiment, the first side element is connected to the central element by means of at least two pulley assemblies. In a preferred embodiment, the second side element is connected to the central element by means of at least two pulley assemblies. In a preferred embodiment, the first side element is connected to the central element by means of at least two pulley assemblies and the second side element is connected to the central element by means of at least two pulley assemblies, wherein the leverage points of the at least four pulley assemblies on the central element are height-adjustable independently from one another by means of detachable mechanical coupling means.

In a preferred embodiment, the tensioning effect of the tensioning device can be achieved by decreasing the distance of the side elements to one another by means of the pulley assemblies.

In a preferred embodiment, the each pulley assembly is individually tensionable and/or releasable. Preferably, the individual pulley assemblies are thus not only height-adjustable independently from one another but also tensionable and/or releasable independently from one another.

In a preferred embodiment, the first side element is thus connected to the central element by means of at least two pulley assemblies, and the second side element is connected to the central element by means of at least two pulley assemblies, wherein the leverage points of the at least four pulley assemblies on the central element are height-adjustable independently from one another by means of detachable mechanical coupling means, and wherein the at least four pulley assemblies are tensionable and/or releasable independently from one another.

In a preferred embodiment, the at least one pulley assembly is designed as single or multiple pulley assembly with at least one pulling cable deflection and one pulling cable anchoring. In a preferred embodiment, the at least one pulley assembly is designed as single pulley assembly. In a preferred embodiment, the at least one pulley assembly is designed as multiple pulley assembly.

In a preferred embodiment, the pulling cables run in a pulling cable tunnel which runs between side element and central element and is made of plastic flexible material. The pulling cable tunnel is preferably resilient. This is advantageous because, in case of a tensioning of the pulling cables, the pulling cable tunnel does not develop or barely develops interfering creases.

In a preferred embodiment, the pulling cable tunnel has an additional tunnel branch in its path between side element and central element, in which the loose end of the pulling cable is guided.

In a preferred embodiment, the side elements are hooked and looped, for example, to a knitted orthosis fabric.

In a preferred embodiment, the central element is designed as backplate such that it can be molded according to the contour of the spinal column anatomy. In an alternative embodiment, the central element is designed as a bridge plate. However, the central element can also be designed such that it can be used as backplate and/or bridge plate.

If the central element is designed as bridge plate, corresponding channels are preferably provided, into which rigid rods can be inserted.

In a preferred embodiment, the central element is designed such that is has a hollow contour along the spinal column, thus avoiding pressure points on the spinal column.

The technical problem is also solved by a tensioning device for an orthosis which is particularly characterized in that it has at least one tensioning segment, particularly at least two, particularly preferred a plurality of separate, particularly substantially parallel, and substantially similar tensioning segments which are adjacent to one another, particularly directly adjoining, wherein these tensioning segments are tensionable independently from one another by means separate pulley assemblies, and the pulley assemblies can be attached individually and height-adjustably to a central element designed as backplate.

Therefore, one embodiment is a tensioning device according to the invention, containing at least one tensioning segment, particularly at least two tensioning segments, preferably a plurality of independently tensionable tensioning segments, each having a first side element on a first end and a second side element on an opposite second end, and a central element arranged in between, wherein the first and the second side element of a tensioning segment are connected to one another by means of the central element of such tensioning segment by at least one first pulley assembly extending between the central element and the first side element, and at least one second pulley assembly extending between the central element and the second side element.

Therefore, one embodiment is a tensioning device according to the invention, containing a plurality of separate, independently tensionable tensioning segments, each having a first side element on a first end and a second side element on an opposite second end, and a central element arranged in between, wherein the first and the second side element of a tensioning segment are height-adjustably connected to one another by means of the central element of such tensioning segment by a first pulley assembly extending between the central element and the first side element, and a second pulley assembly extending between the central element and the second side element.

Preferably, the first and the second side element of a tensioning segment are connected to one another by means of the central element of such tensioning segment by a first pulley assembly extending between the central element and the first side element, and a second pulley assembly extending between the central element and the second side element.

The side elements, the central element, and the pulley assemblies of a tensioning segment are preferably designed as described above.

The tensioning segments each have a first side element on a first end of the tensioning device, and a second side element on an opposite second end of the tensioning device. A central element is preferably centrally arranged between the first and the second side element. The side elements are mechanically connected to one another by means of the central element, each namely by means of at least one first pulley assembly, preferably extending between the central element and the first side element, and at least one second pulley assembly, preferably extending between the central element and the second side element, said side elements thus forming a tensioning segment.

Preferably, the central elements of the tensioning segments are connected to one another.

Preferably, the central elements of the at least two, particularly the plurality of tensioning segments, are connected to one another by means of connection elements. Alternatively, the central elements of the tensioning segments together can also form one long, one-piece central element.

The central elements of the at least two, particularly the plurality of tensioning segments, can be connected to one another, for example, by means of bars, tracks, or tubes, for example, made of metal, particularly aluminum or plastic. Of course, screw connections, snap connections, or hook connections between every two central elements are also possible. The central elements of at least two tensioning segments can be connected to one another rigidly or flexibly, for example, by means of a joint.

It is self-evident that the central elements of the at least two, particularly the plurality of tensioning segments, are connected to one another on top of one another, i.e., the central element of the uppermost and the bottommost tensioning segment is each connected to a corresponding further central element, and in case of at least three tensioning segments, the at least one central element positioned in between is connected to two further central elements.

However, the central elements of the at least two, particularly the plurality of tensioning segments, can also not be directly connected to one another but be connected by means of the pulley assemblies and/or the back orthosis.

In the applied state, the tensioning device in conjunction with the orthosis is applied around the body part, and the two ends of the tensioning device are connected in a force-locking manner; the tensioning device is closed similar to a belt around the body part. Within a single tensioning segment, the invention provides at least one pulley assembly on each of the two sides of a central element, said pulley assembly extending to the side elements. The pulley assemblies of a tensioning segment positioned opposite each other can be tensioned circularly during the use of the applied orthosis by pulling on both sides of the loose ends of their two pulling cables in opposite direction. During tensioning, the distance between the side elements and thus the two ends of the tensioning device is shortened, thus generating a circular tension surrounding the body part. Advantageously, this results in a force effect symmetrical to the central element. The circular tension can thus act directly, symmetrically evenly on both sides of the central element, and so the central element is not shifted from its position during tensioning. A warping or shifting of the tensioning device or the orthoses connected to the tensioning device is effectively prevented during tensioning.

In a preferred embodiment, the central element of a tensioning segment has at least two coupling means, positioned one above the other, for the first pulley assembly for connecting the first side element, and at least two coupling means, positioned one above the other, for the second pulley assembly for connecting the first side element. Particularly preferred, the central element of a tensioning segment has at least three coupling means, positioned one above the other, for the first pulley assembly for connecting the first side element and at least three coupling means, positioned one above the other, for the second pulley assembly for connecting the first side element.

Preferably, the central element of a tensioning segment has three, four, five, six, or seven coupling means, positioned one above the other, for the first pulley assembly for connecting the first side element, and three, four, five, six, or seven coupling means, positioned one above the other, for the second pulley assembly for connecting the first side element.

In an embodiment according to the invention, pulley assemblies are designed with multiple deflections. Each of the pulley assemblies is anchored on the central element and the first or second side element of one and the same tensioning segment. The pulley assembly of a tensioning segment has no anchoring or deflection points on another, particularly adjacent tensioning segment. According to the invention, each tensioning segment thus has its own pulley assemblies which are separate from the other tensioning segments.

In a departure from the prior art, the invention also provides for a plurality of pulley assemblies arranged preferably substantially parallel and independently in separate tensioning segments. Each pulley assembly engages exclusively with its associated central element and side elements of a tensioning segment, wherein the point of application on the central element is height-adjustable. Therefore, in this embodiment, one individually adjustable pair of pulley assemblies is preferably associated with each individual tensioning segment. Each pulley assembly, in conjunction with the opposite pulley assembly which faces the other end, allows a segmental, individually adjustable, symmetrical, circular tensioning effect, wherein said tensioning effect can be directed individually and purposefully to a specific point of the central element due to the height-adjustability with regard to the central element.

For realizing the pulling cable drive in the form of a pulley assembly, the invention preferably provides on the central element toward both sides per segment preferably exactly one pulling cable deflection element each for deflecting the pulling cable of the corresponding pulley assembly, or optionally or additionally, preferably exactly one anchoring of the end of the pulling cable. The invention thus prevents an equalizing of the force effect of a pulley assembly over larger sections or the entire width of the orthosis belt with a plurality of known adjacent pulling cable deflection elements or anchorings of the pulling cable. Instead, the pulley assembly according to the invention has preferably exactly one anchoring point each with the central element and the side element of the tensioning segment; the anchoring point is designed as pulling cable deflection element, preferably as deflecting roller, or as anchorings point, in which the pulling cable is stationarily fastened. According to the invention, force is thus preferably applied per tensioning segment on a single force application point by means of the pulley assembly. Depending on the design of the pulley assembly, the force application point is designed as pulling cable deflection or, alternatively or additionally, as pulling cable anchoring. In a particular embodiment of the invention, at least two optional anchoring points, spaced apart from one another, are provided on the central element and/or the side element, and said anchoring points can each be selected as alternative force application points for individual adjustment of the tensioning device.

In a particular embodiment, the tensioning device has at least two, preferably three or four or five, separately tensionable tensioning segments. Preferable variations have exactly three, four, or five adjacent tensioning segments, each with an associated pair of pulley assemblies. These variations are thus separately tensionable on three, four, or five segments.

The segmental application of force into a single force application point within a segment allows for a vertebral segment-specific application of force, particularly in conjunction with the use of the tensioning device on or in a back orthosis. Preferably, in this embodiment of the invention, at least one vertebra or a vertebra group is associated with one tensioning segment. Preferably, a single tensioning segment generates a predominant application of force on or within the region of precisely one vertebra or vertebra section, and another tensioning segment generates a predominant application of force on or within the region of precisely one other vertebra or vertebra section.

In a particular embodiment, at least one tensioning segment additionally has, preferably on or in the region of its central element, at least one truss pad facing the body part, preferably made of elastic padding material, for the segmental application of force according to the invention. This truss pad is preferably designed such that it directs the application of force of said tensioning segment purposefully to a specific body region. In a preferred variation, the truss pad can be individually added to or removed from the tensioning device. Preferably, with regard to its form and/or material, the truss pad is exchangeable and/or adjustable on the tensioning segment for modification of the effect of facilitating. In a particular variation, a tensioning segment can have an associated truss pad which, in conjunction with the purposefully adjustable application of force of the tensioning segment, individually massages and stimulates specific soft tissue structures of the body part. For example, a trigger point of a muscle can thus be purposefully stimulated, e.g., in order to achieve a purposeful tensioning or relaxing of the muscle. Such purposefully, segmentally adjustable and triggerable applications on the body part are not achievable with known tensionable orthoses.

Preferably, the truss pad is adjustably attachable, particularly height-adjustable, and so the truss pad is positioned on the central element at the selected point of application of at least one pulley assembly.

A particular embodiment additionally provides that at least two adjacent tensioning segments of the tensioning device are mechanically connected to one another. For such purpose, a rigid coupling is preferably provided. Alternatively, a flexible coupling, particularly in the form of a flexible, e.g. elastic, strap is preferred. In a particular embodiment thereof, at least the side elements of two directly adjacent segments are mechanically connected to one another in order to form at least one integral side bridge from at least two side elements. In a particular embodiment, the side elements of all present segments are connected to one another in this manner, forming a single side bridge. In a particular variation, the side bridges are designed as one piece.

In a particular embodiment thereof, at least the central elements of two directly adjacent segments are, alternatively or additionally, mechanically connected to one another in order to form at least one integral central bridge from at least two central elements. In a particular embodiment, the central elements of all present segments are connected to one another in this manner, forming a single central bridge. The central bridge can be designed as one piece.

In a particular embodiment, the integral central bridge additionally has at least one support element for a body part, extending perpendicularly to the direction of force of the pulley assemblies, or consists of such a support element. This support element is designed to be on or in the central element or is designed as central element. The support element is made of a comparatively inelastic, tough, and brittle material. The support element can be designed in the form of a simple rod, for example as individual moldable metal rod or thermoplastically moldable plastic rod. Due to the segmentally applicable tensioning force according to the invention, this support element can be applied individually to the body part in order to facilitate the support function or the therapeutic formative function. In particular, this support element is formed in an anatomically and therapeutically practical manner and directly supports a body part, particularly the spinal column, i.e., in a back orthoses, for example, the support element extends along the spinal column, thus supporting the spinal column.

Alternatively, instead of a single support rod, two rod-shaped support elements, spaced apart from one another, are provided which are connected to one another by means of transverse bridges formed between recesses of the central element. Particularly in case of a back orthosis, the spinal column can thus be supported directly to the left and right of the spinal ridges; a direct pressure load of the spinal ridges is prevented.

In a particular embodiment, the invention provides for the pulling cables of the pulley assembly of a first tensioning segment each to be guided together, but separately and spaced apart from the pulling cables of the pulley assembly of an adjacent second segment. In a particular embodiment, a grid frame is provided for such purpose which is arranged between the central elements and side elements and which holds the pulling cables of a pulley assembly together and spaced apart and separate from the pulling cables of another pulley assembly. For such purpose, the pulling cables are appropriately guided through the meshes of the grid frame. It is preferably provided that, particularly in case of a back orthosis, the grid frame is also designed as stabilizing pelvis harness which acts rotationally stabilizing.

In a particular embodiment of the invention, the pulling cables of a pulley assembly are guided in a pulling cable tunnel. The pulling cable tunnel preferably extends between the side element and the central element. The pulling cable tunnel is preferably made of a plastic flexible material; an elastic knitted fabric is particularly preferred. The invention thus allows for a compact and user-friendly realization of the segmental individual pulley assemblies. It is thus effectively prevented that contact is made with pulling cables of adjacent pulley assemblies, and pieces of clothing or other orthosis components are caught.

In a particular variation of this embodiment, the pulling cable tunnel additionally has a tunnel branch, which branches off in the path between side element and central element. The loose end of the pulling cable of a pulley assembly can be guided in said tunnel branch. The loose end can be guided through the tunnel branch, which, similar to the pulling cable tunnel, can be made of a plastic or flexible material, such that the twisting or knotting with the pulling cable ends of adjacent pulley assemblies is prevented and the use of the tensioning device during application and tensioning is simplified. In an alternative or additional embodiment, the pulling cables of the pulley assemblies are each guided separately in a spacer fabric.

In a particular embodiment, the pulling cables are directly placed in the knitted fabric of an orthosis. For such purpose, the knitted fabric of the orthosis preferably has tunnel-shaped recesses or tabs which allow for the pulling cables to be guided separately. Additional measures, such as grid frames provided in the previously described embodiment for spacing apart the pulling cables of adjacent pulley assemblies are not required in this embodiment. In the simplified embodiment of a tensioning device according to the invention which is already integrated in the knitted fabric orthosis, the ability to add or remove the tensioning device on an upright, particularly a conventional orthosis, particularly a knitted fabric orthosis, as described herein, is not required; instead, the tensioning device according to the invention is an integral component of a corresponding new type of a herein described orthosis according to the invention.

In a particular embodiment, the loose end of a pulling cable runs into a handle, in which it is secured. By means of the handle, the user can tension the loose end of the pulling cable of a pulley assembly. The handle is designed to be detachably securable in the region of the side element connected with the pulley assembly, i.e. in the region of the corresponding ends of the tensioning device, in order to maintain tension. For preadjusting the tensioning length of the pulling cable end, the handle piece can have a clamping device, with which the "operating point" of each pulley assembly can be adjusted segmentally in order to ensure the individual adjustment of the orthosis. The handle is temporarily secured on the tensioning device in a known manner by hook-and-loop or linking means.

Instead of a non-stationarily securable handle, a preferably detent roll-up mechanism for the corresponding pulling cables can alternatively be provided in the region of the side elements.

The side elements and/or the central element have connection means in order to be connected, possibly detachably, to the orthosis. The invention thus also allows for an adding or removing of the tensioning device to or from an existing orthosis. In particular, the existing orthosis is a conventional knitted fabric orthosis, particularly a rod orthosis, which, due to its intrinsic elasticity, is applied around the body part and closed in a known manner by means of tabs. In case of a back orthosis, the tensioning device according to the invention can be attached to the orthosis in the region of the dorsal side and the hip side.

The tensioning device according to the invention allows for an individual and precisely accurate adjustment of the tensioning force of an orthosis over a wide region. Since the stabilizing or securing effect of the orthosis is substantially entirely taken over by the tensioning device itself, a subjacent elastic knitted fabric orthosis, which is designed in a known manner, no longer has to apply a complete tensioning or supporting effect. Advantageously, a knitted fabric can thus be used which can be applied over a wide circumferential region—in case of a back orthosis, for example, on a slender waist as well as big abdominal or chest girth—without having to provide knitted fabric orthoses which are individually adjusted to the size of the body. The adjustment to the girth can preferably be made exclusively by adjusting the pulley assemblies, thus particularly by means of the segmental adjustment of the "operating points" of the loose ends of the pulley assemblies.

The present invention also relates to a backplate for a back orthosis, wherein the backplate, to the left and right of an imaginary center line, has at least two, preferably at least three superimposed coupling elements, wherein the coupling elements are suitable for the detachable coupling of a pulley assembly.

Particularly, the backplate can be a central element of a tensioning device according to the invention, of a tensioning segment according to the invention, of a plurality of tensioning segments according to the invention, or of an orthosis according to the invention. As already described for a central element, tensioning forces can be applied individually and precisely with the backplate according to the invention, for example, by connecting at least one first pulley assembly with a selected left coupling element, and at least one second pulley assembly with a selected right coupling element.

In a preferred embodiment, the backplate has at least two backplate segments which are connected to one another by means of connection elements. The backplate segments can be connected to one another, for example, by means of rods, tracks, or tubes, for example, made of metal, particularly aluminum or plastic. Of course, screw connections, snap connections, or hook connections between every two central elements are also possible. The backplate segments can be connected to one another rigidly or flexibly, for example, by means of a joint.

In a preferred embodiment, the coupling elements are holes for engaging or latching of a coupling counter element of a pulley assembly.

The present invention also relates to an orthosis, containing a tensioning device according to the invention.

The present invention also relates to the use of a tensioning device according to the invention for segmental and positionally accurate control of the tensioning or support function of an orthosis.

Further embodiments can be readily derived by a person skilled in the art from DE 10 2010 035 309 A1.

BEST DESCRIPTION OF THE DRAWING

The invention shall be described in further details by the following drawings and drawing descriptions. They shall not be considered to be delimiting.

Figure 1:
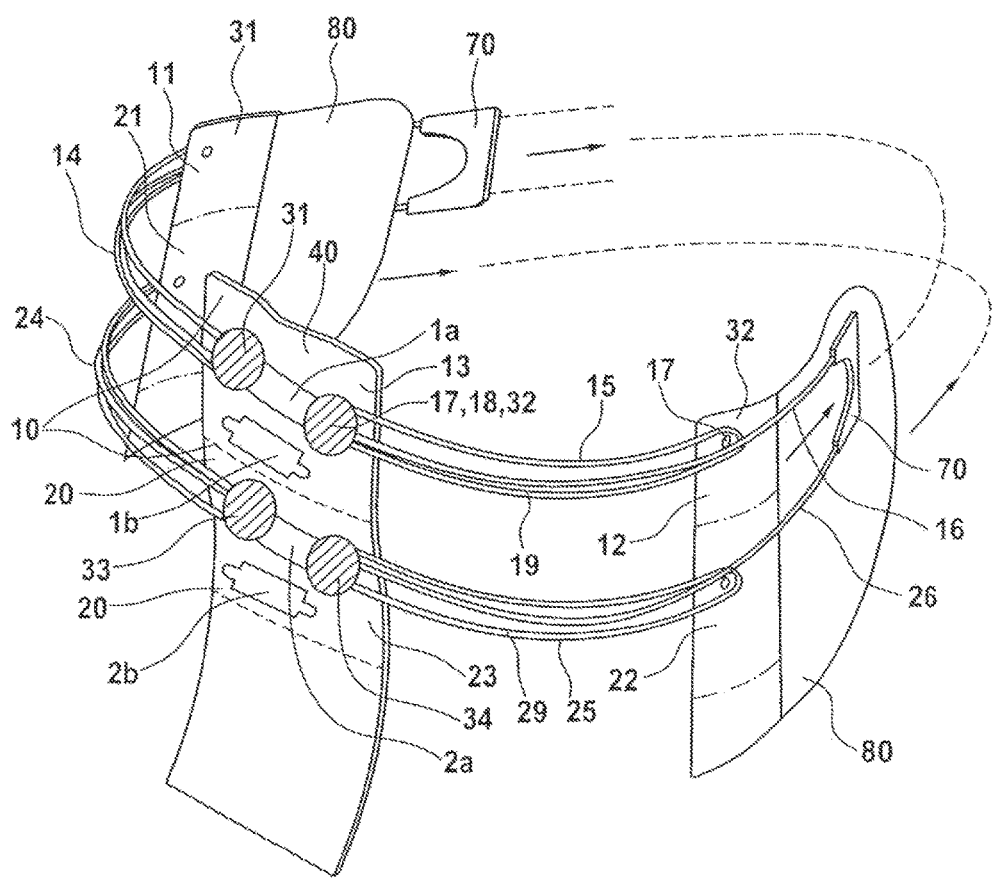
FIG. 1 shows an embodiment of a tensioning device according to the invention.
Figure 2:
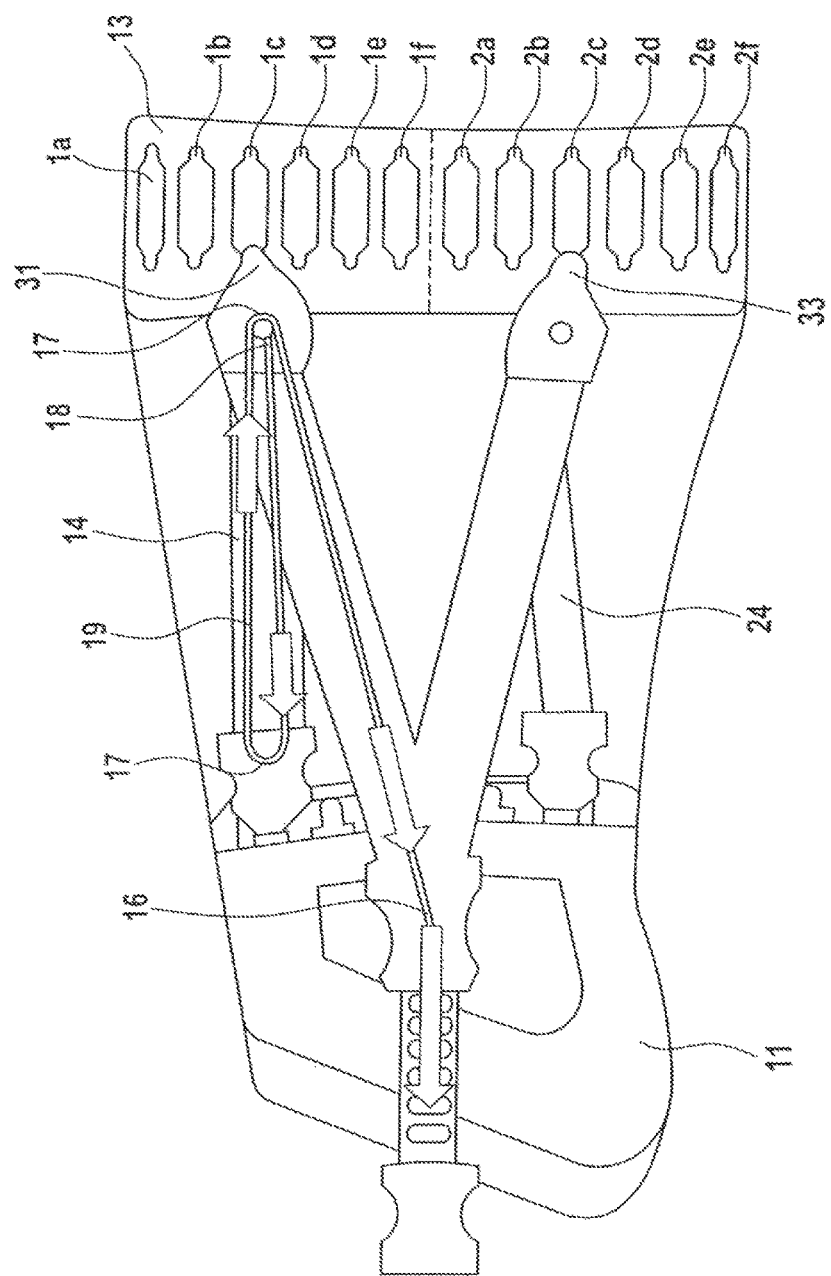
FIG. 2 shows a section of an embodiment of a tensioning device according to the invention.

As shown in FIGS. 1-3, the pulley assemblies may be attached to the central element by mounting suspension elements of the pulley assemblies in recesses of the central element. As illustrated in FIG. 4, the pulley assemblies may be alternatively attached to the central element by mounting suspension elements of the central element in recesses of the pulley assemblies.

DETAILED DESCRIPTION

FIG. 1 shows an embodiment of the tensioning device according to the invention, adjusted for use on a back orthosis for stabilizing the spinal column. For reasons of clarity, the view does not completely show all recurring structures. Per tensioning segment (10), two pulling cable drives (14, 15) in the form of pulley assemblies are each connected to the left and right of the central element (13), which are each mechanically connected to the side element (11), depicted on the left side and in the background, and the second side element (12), depicted on the right side and in the foreground. Each of the pulley assemblies (14, 15) have pulling cables (19), pulling cable deflections (17) and pulling cable anchorings (18) in order to form one multiple pulley assembly each. Per tensioning segment, the pulley assemblies (14, 15) are thus anchored each in precisely one force application point (17, 18) on the central element (13) and the side element (11, 12). In the drawing, the side elements, connected to form side bridges (31, 32) and the central elements, connected to form a central bridge (40), are distinguishable from one another by means of dividing lines. The pulley assemblies (14, 15) of the first tensioning segment (10) each have loose cable ends (16), with which the pulley assemblies can be tensioned, thus shortening the distance between the central element (13) and the side elements (11, 12) for tensioning purposes.

Correspondingly, the adjacent tensioning segments (20) have pulley assemblies (24, 25) with pulling cables (29) and loose ends (26). Each of the pulley assemblies (24, 25) connect the corresponding first and second side elements (21, 22) with one another by means of the central element (23). Pulley assembly 14 may be a first pulley assembly. Pulley assembly 24 may be a second pulley assembly. Pulley assembly 15 may be a third pulley assembly. Pulley assembly 25 may be a fourth pulley assembly.

The present embodiment according to the invention is characterized in that the leverage points, i.e. the force application points of the pulley assemblies (14, 15, 24, 25) on the central elements (13, 23) of the tensioning segments (10, 20) are height-adjustable by means of detachable mechanical coupling means. The mechanical coupling means comprise elongated holes (1a, 1b, 2a, 2b) with narrowed ends located in the central elements (13, 23), and coupling elements (31, 32, 33, 34) which are designed as pulling cord deflection (17) and pulling cord attachment (18), and which can be mounted in the elongated holes (1a, 1b, 2a, 2b) of the central elements (13, 23) by means of a latching element. The coupling elements (31, 32) of the first tensioning segment (10) can be mounted, independently from one another, either in the upper elongated hole (1a) of the first tensioning segment (10) or in the lower elongated hole (1b) of the first tensioning segment (10). The coupling elements (33, 34) of the second tensioning segment (20) can be mounted, independently from one another, either in the upper elongated hole (2a) of the second tensioning segment (20) or in the lower elongated hole (2b) of the second tensioning segment (20). Thus, according to the invention and advantageously, the force application points of the individual pulley assemblies (14, 15, 24, 25) are height-adjustable on the central elements (13, 23) and can therefore act in a selected region. Of course, a segment can also have more than two elongated holes, for example, three to six elongated holes, allowing for the height-adjustability to be even more variable and precise.

The separate tensioning segments (10, 20), which are positioned one below the other, are mechanically coupled with one another. The first side element (11) of the first tensioning segment (10) is coupled with the first side element (21) of the second tensioning segment (20), forming a common one-piece side bride (31). Correspondingly, the second side element (21) of the first tensioning segment is coupled with the second side element (22) of the second tensioning segment (20), forming a one-piece side bride (32). Similarly, the central element (13) of the first tensioning segment (10) is coupled with the central element (23) of the second tensioning segment to form a one-piece central bridge (40). Despite the mechanical coupling of mechanical tensioning segments (10, 20) with one another by means of the side bridges (31, 32) and the central bridge (40), a segmental, individual adjustment of the tensioning force is possible by means of the separately guided pulley assemblies.

In the embodiment as back orthosis, the central bridge (40) forms an anatomically moldable spinal column support which, in the applied state of the orthosis, is placed on or in the region of the spinal column.

The loose ends (16, 26) on the left and right side of the pulley assemblies of individual tensioning segments (10, 20) run, spaced apart from one another, into a common handle (70). The handle (70) is detachably securable in the region of the side elements/side bridges (11, 12, 31, 32). By pivoting the handle (70) during securing, the tensioning force can be distributed individually onto the two tensioning segments. In the depicted embodiment, the formed side bridges (31, 32) each end in closure tabs (80) which are connected in a force-locking manner, when the orthosis is applied to the body in the form of a belt or a bandage, thus achieving the segmental circular force lock according to the invention.

FIG. 2 schematically shows a section from a further embodiment of the tensioning device according to the invention. For reasons of clarity, the view only shows a side element (11) and the central element (13). The second side element would connect to the other half of the central element similarly to the first side element, only mirrored. The side element (11) is mechanically connected to the central element (13) by means of two pulling cable drives (14, 24) in the form of pulley assemblies. The pulley assemblies (14, 24) each have pulling cable deflections (17) and pulling cable anchorings (18) for a pulling cable (19) in order to form one multiple pulley assembly each. Per tensioning segment, the pulley assemblies (14, 15) are thus anchored each in one force application point (17, 18) on the central element (13) and the side element (11). The pulley assemblies (14, 24) each have loose cable ends (16), by means of which the pulley assemblies can be tensioned, thus shortening the distance between the central element (13) and the side element (11) for tensioning purposes.

The present embodiment according to the invention is characterized in that the leverage points, i.e. the force application points of the pulley assemblies (14, 24) on the central element (13) of the tensioning segments, are height-adjustable by means of detachable mechanical coupling means. The mechanical coupling means comprise elongated holes (1a to 1f, 2a to 2f) located in the central elements (13, 23) with narrowed ends and coupling elements (31, 33) which are designed as pulling cord deflection (17) and pulling cord attachment (18), and which can be mounted in the elongated holes (1a to 1f, 2a to 2f) of the central element (13) by means of a latching element. The coupling element (31) can be mounted in one of the upper elongated holes (1a to 1f). The coupling element (33) can be mounted in one of the lower elongated holes (2a to 2f). Thus, according to the invention and advantageously, the force application points of the individual pulley assemblies (14, 24) are height-adjustable on the central element (13) and can therefore act in a selected region. A person skilled in the art would readily discern that a second side element can be connected to the central element (13) in the same manner.

Figure 3A:
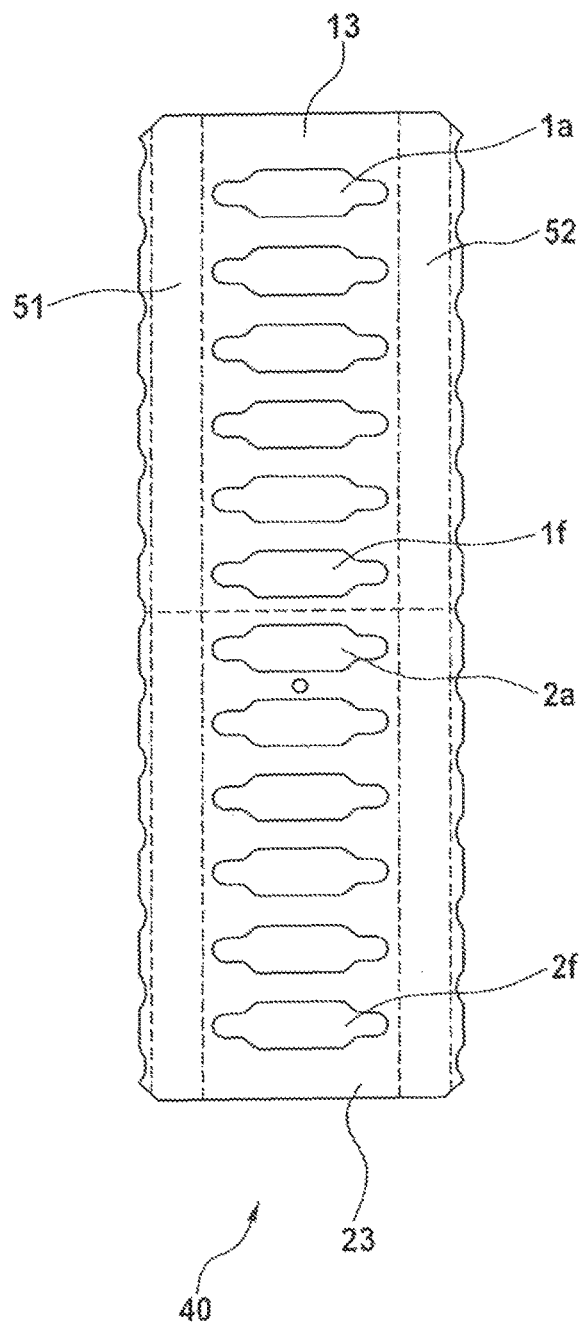
FIGS. 3a to 3c show different embodiments of a backplate according to the invention, or a central element according to the invention.
Figure 3B:
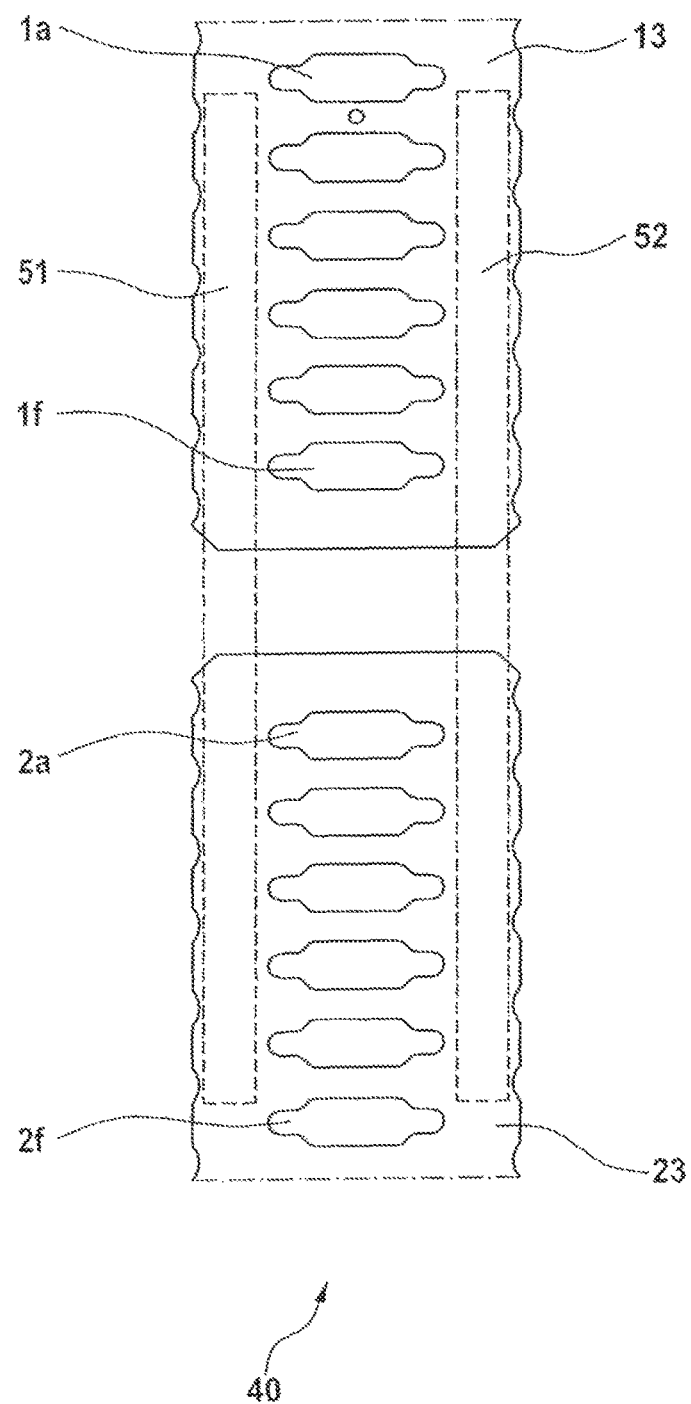
Figure 3C:
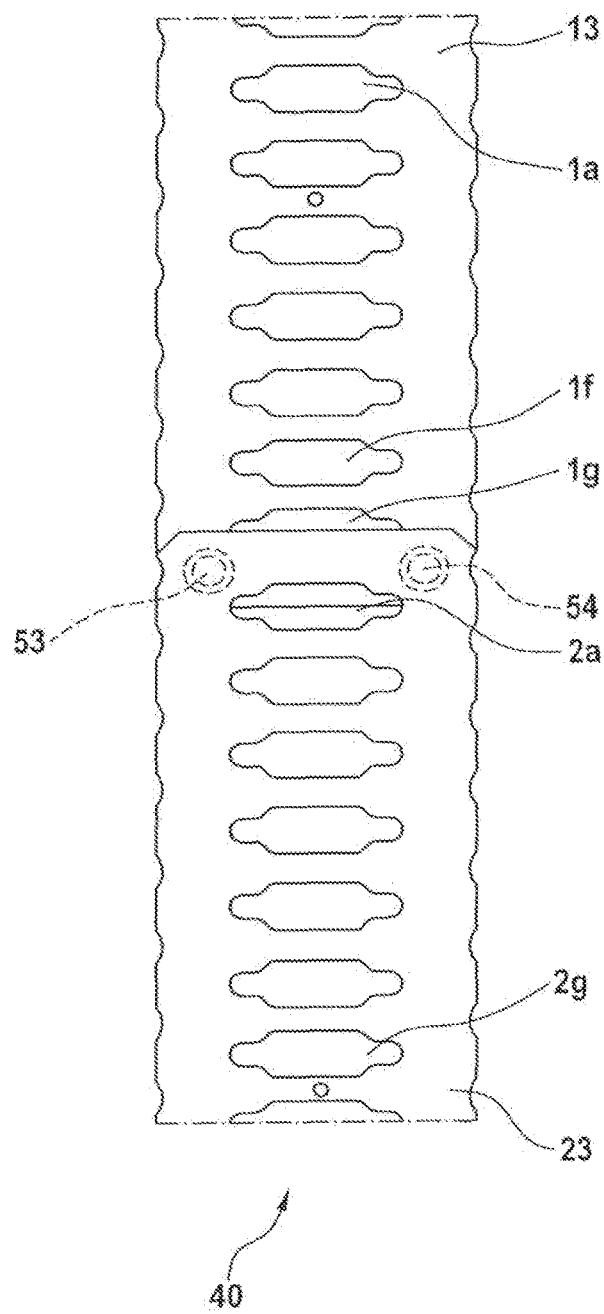
Figure 4:
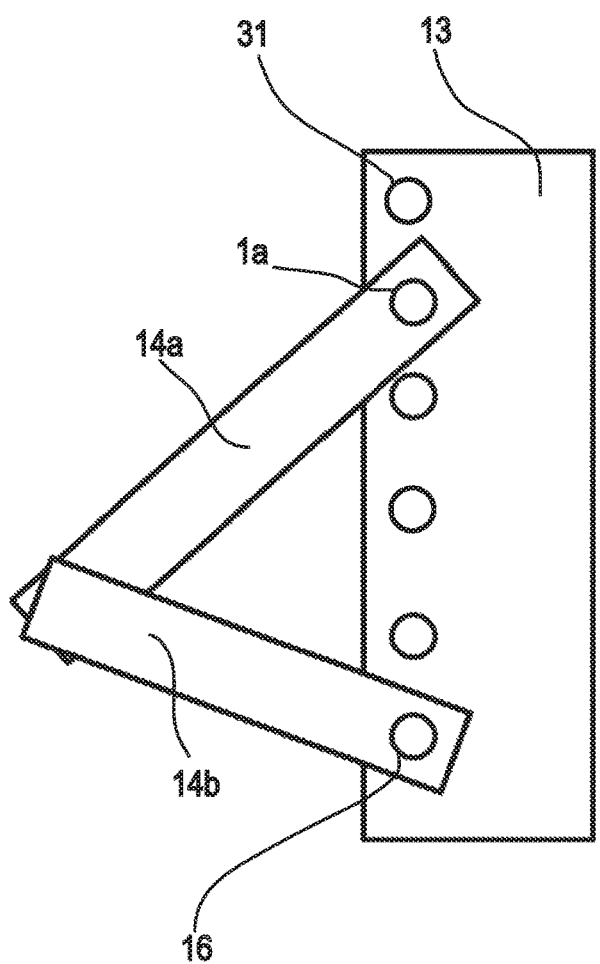
FIG. 4 is a schematic view illustrating an alternative arrangement in which the pulley assemblies include the plurality of contact points and the central element includes the plurality of openings.

FIGS. 3a to 3c show different embodiments of a backplate or central bridge (40) with two central elements (13, 23). All central elements have elongated holes (1a to 1f, 2a to 2f) with narrowed ends, in which the coupling elements of a pulley assembly can be mounted or engaged. In FIG. 3a, the two central elements (13, 23) are designed together as one piece. They are reinforced with two aluminum rods or tubes (51, 52). In FIG. 3b, the two central elements (13, 23) are separated and spaced apart from one another and connected to one another by means of the two aluminum rods or tubes (51, 52). In FIG. 3c, the two central elements (13, 23) are separate from one another, but overlap to some extent, and are connected to one another by means of two connection elements (53, 54), for example, clips or screw connections. The central elements have additional elongated holes (1g, 2g). In the region of overlap of the two central elements (13, 23), the elongated holes (1g, 2a) are not suitable for mounting the coupling elements in this embodiment.

The invention claimed is:

1. A tensioning device for an orthosis comprising:
at least one first side element;

at least one second side element; and
at least one interjacently arranged central element including one of a plurality of openings and a plurality of contact points;
a plurality of pulley assemblies including a least a first pulley assembly, a second pulley assembly, a third pulley assembly and a fourth pulley assembly,
the first pulley assembly and the second pulley assembly connecting and running between the central element and the first side element,
the third pulley assembly and the fourth pulley assembly connecting and running between the central element and the second side element;
an arrangement for connecting the first, second, third and fourth pulley assemblies along a length of the central element, the arrangement including a plurality of openings having openings and a plurality of contact points, the plurality of contact points including first, second, third and fourth contact points,
wherein the openings of the plurality of openings are selectively engageable with the contact points of the plurality of contact points such that the first, second, third and fourth pulley assemblies are independently adjustable from one another the length of the central element, and
wherein either:
  i) the plurality of pulley assemblies includes the plurality of contact points and the central element includes the plurality of opening along the length of the central element; or
  ii) the central element includes the plurality of contact points along the length of the central element and the plurality of pulley assemblies includes the plurality of openings.

2. The tensioning device according to claim 1, further comprising at least first and second separate, independently tensionable tensioning segments, the first tensioning segment including the first and third pulley assemblies, the second tensioning segment including the second and fourth pulley assemblies, each tensioning segment having the first side element on a first end and the second side element on an opposite second end, and the central element arranged in between.

3. The tensioning device according to claim 2, wherein each tensioning segment is connected to the central element with at least two elongated holes, positioned one above the other, and connected to a respective one of the first and second side elements with at least two further elongated holes, positioned one above the other.

4. The tensioning device according to claim 2, wherein the central elements of the plurality of tensioning segments are connected to one another by connection elements selected from a group consisting of rods, screw connections, snap connections and hook connections.

5. The tensioning device according to claim 1, wherein a tensioning effect of the tensioning device is achieved by decreasing a distance of the first and second side elements to one another by the first, second, third and fourth pulley assemblies.

6. The tensioning device according to claim 1, wherein the pulley assemblies are designed as single or multiple pulley assembly with at least one pulling cable deflection and one pulling cable anchoring.

7. The tensioning device according to claim 1, in combination with an orthosis.

8. A method of tensioning an orthosis with a tensioning device, the tensioning device having:
at least one first side element;
at least one second side element; and
at least one interjacently arranged central element including one of a plurality of openings and a plurality of contact points;
a plurality of pulley assemblies including at least a first pulley assembly, a second pulley assembly, a third pulley assembly and a fourth pulley assembly;
the first and second side elements connected to one another by the central element,
the first pulley assembly and the second pulley assembly running between the central element and the first side element,
the third pulley assembly and the fourth pulley assembly running between the central element and the second side element;
an arrangement wherein the openings of the plurality of openings are selectively engageable with the contact points of the plurality of contact points such that the first, second, third and fourth pulley assemblies are independently adjustable from one another along a length of the central element, and
wherein either:
  iii) the plurality of pulley assemblies includes the plurality of contact points and the central element includes the plurality of opening along the length of the central element; or
the central element includes the plurality of contact points along the length of the central element and the plurality pulley assemblies includes the plurality of openings,
the method comprising:
selectively engaging the first and second contact points with respective openings of the plurality of openings; and
segmentally controlling tensioning and support of the orthosis with the tensioning device.

9. The tensioning device according to claim 2, wherein the first and second pulley assemblies each have loose cable ends for shortening a distance between the central element and a respective one of the first and second side elements for tensioning.

10. The tensioning device according to claim 1, wherein adjacent tensioning segments have pulley assemblies with pulling cables and loose ends, the adjacent tensioning segment connecting the corresponding first and second side elements with one another through the central element.

11. The method according to claim 8, further comprising independently adjusting the first, second, third and fourth contact points on the central element along the length of the central element.

12. The method according to claim 8, wherein the first and second pulley assemblies include loose cable ends and the method comprises pulling the loose cable ends to shorten a distance between the central element and a respective one of the first and second side elements.

13. The tensioning device according to claim 1, wherein first and third pulley assemblies disposed in a first horizontal plane and the second and fourth pulley assemblies are disposed in a second horizontal plane, the first d horizontal plane spaced from the second horizontal plane along the length of the central element.

14. The tensioning device according to claim 3, wherein the at least two elongated holes are spaced apart from one another along the length of the central element.

15. The method according to claim 8, wherein first and third pulley assemblies disposed in a first horizontal plane and the second and fourth pulley assemblies are disposed in a second horizontal plane, the first horizontal plane spaced from the second horizontal plane along a length of the orthosis.

16. The method according to claim 8, wherein the tensioning device further includes at least first and second separate, independently tensionable tensioning segments, the first tensioning segment including the first and third pulley assemblies, the second tensioning segment including the second and fourth pulley assemblies, each tensioning segment having the first side element on a first end and the second side element on an opposite second end, and the central element arranged in between, wherein each tensioning segment connected to the central element with at least two elongated holes, positioned one above the other, and connected to a respective one of the first and second side elements with at least two further elongated holes, positioned one above the other, and wherein the at least two elongated holes are spaced apart from one another along a length of the orthosis.

* * * * *